United States Patent [19]

Miyauchi et al.

[11] Patent Number: 5,888,755

[45] Date of Patent: *Mar. 30, 1999

[54] METHOD OF DETERMINING THE AMOUNT OF CHOLESTEROL IN A HIGH-DENSITY LIPOPROTEIN

[75] Inventors: Kazuhito Miyauchi; Akira Miike, both of Shizuoka; Eiko Shutoh, Ohita; Hiroyuki Sugiuchi, Kumamoto; Tetsumi Irie, Kumamoto; Kaneto Uekama, Kumamoto; Susumu Ohsawa, Yotsukaido, all of Japan

[73] Assignee: Kyowa Medex Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 966,646

[22] Filed: Nov. 10, 1997

Related U.S. Application Data

[62] Division of Ser. No. 545,722, Nov. 2, 1995, Pat. No. 5,691,159.

[30] Foreign Application Priority Data

| Mar. 8, 1994 | [JP] | Japan | 6-037328 |
| Sep. 12, 1994 | [JP] | Japan | 6-217224 |
| Nov. 30, 1994 | [JP] | Japan | 6-296137 |

[51] Int. Cl.$^6$ ............... C12Q 1/60; C12Q 1/44; C12Q 1/26; C12Q 1/28
[52] U.S. Cl. ............... 435/11; 435/19; 435/25; 435/26; 435/28; 435/4; 435/12; 435/10
[58] Field of Search ............... 435/11, 19, 25, 435/26, 28, 4, 12, 10

[56] References Cited

U.S. PATENT DOCUMENTS

| 4,215,993 | 8/1980 | Sanders | 435/11 |
| 4,414,326 | 11/1983 | Goldberg | 435/11 |
| 4,521,519 | 6/1985 | Draeger et al. | 435/11 |
| 4,892,815 | 1/1990 | Kerscher et al. | 435/11 |
| 5,385,828 | 1/1995 | Aufenanger | 435/11 |

FOREIGN PATENT DOCUMENTS

| 0428980 | 5/1991 | European Pat. Off. |
| 62-69999 | 3/1987 | Japan. |
| 126498 | 5/1988 | Japan. |
| 6-037328 | of 1994 | Japan. |
| 6-217224 | of 1994 | Japan. |
| 6-296137 | of 1994 | Japan. |
| 242110 | 9/1994 | Japan. |
| 9201498 | 2/1992 | WIPO. |

OTHER PUBLICATIONS

The 7th International Cyclodextrins Symposium; Tokyo '94; Proceedings; Apr. 25–28, 1994; pp. 532–535.

*Primary Examiner*—Louise N. Leary
*Attorney, Agent, or Firm*—Antonelli, Terry, Stout & Kraus, LLP

[57] ABSTRACT

Provided is a method of determining the amount of cholesterol in high-density lipoprotein (HDL), which comprises reacting an HDL-containing sample with cholesterol esterase and cholesterol oxidase or cholesterol dehydrogenase in the presence of a reagent for aggregating lipoproteins- except HDL, and determining the amount of hydrogen peroxide or reductive co-enzyme formed therein.

40 Claims, No Drawings

METHOD OF DETERMINING THE AMOUNT OF CHOLESTEROL IN A HIGH-DENSITY LIPOPROTEIN

This is a division of application Ser. No. 08/545,722, filed Nov. 2, 1995, now U.S. Pat. No. 5,691,159.

TECHNICAL FIELD

The present invention relates to a method of-determining the amount of cholesterol in a high-density lipoprotein (HDL)[hereinafter referred to as "HDL cholesterol"]. HDL is important in lipid metabolism in the field of clinical diagnosis.

BACKGROUND ART

It is known that HDL is related to the removal of cholesterol accumulated in cells for receiving cholesterol from tissues including arterial walls, that HDL is a negative risk factor of various types of arteriosclerosis such as coronary arteriosclerosis, and that HDL level in blood is an index useful for the precognition of arteriosclerosis. The conventional method of determining the amount of HDL cholesterol consists of two steps, a fractionation step and a step of determining the amount of cholesterol. Examples of the fractionation include an ultracentrifugation method, an immunochemical method, an electrophoretic method and a precipitation method. In the ultracentrifugation method, HDL is separated through specific gravity using an ultracentrifuge to determine the amount of HDL cholesterol. However, this method is defective in precision in determination, complexity and economical efficiency. The immunochemical method includes an immunoelectrophoretic method, a single radial immunodiffusion (SRID) method, and an Ouchterlony diffusion method. However, these methods are defective in that an apoprotein is recognized but a lipoprotein is not exactly recognized. In the electrophoretic method, a cellulose acetate film or an agarose gel is separated as a support, and the amount of cholesterol is enzymatically determined. This method is defective in simplicity and economical efficiency. In the precipitation method, polyethylene glycol or a polyanion such as heparin, phosphotungstic acid and dextran sulfuric acid, and a divalent cation are bound to an apoprotein B, which is present on surfaces of low-density lipoprotein (LDL), very-low-density lipoprotein (VLDL) and chylomicron (CM) to form an insoluble precipitate, and this insoluble precipitate is removed by centrifugation to determine the amount of HDL cholesterol in the supernatant (Summary of Clinical Investigation Method, 29th edition, Kanai I., Kanehara Shuppan, p. 471, 1983). This method is the simplest. However, this method is not suitable in case of using an autoanalyzer which is often used in the measuring a large number of specimens, for rapid measurement and in clinical investigation, since this method involves centrifugation step by a centrifuge. Further, in the fractionation, a mannual error tends to occur, for example, when the amount of the HDL fraction separated is determined using a measuring pipet. Thus, the complexity of the determination of the amount of HDL cholesterol lies in the fractionation procedure. However, if a serum specimen is directly added to a reagent containing a cholesterol esterase and a cholesterol oxidase without fractionating HDL, this method is not different from a system of determining the total amount of cholesterol, and the amount of HDL cholesterol cannot be specifically determined by this method. Japanese Published Unexamined patent application No. 126,498/1988 describes that a cholic acid is added to increase the specificity. However, in this prior art method, not only HDL but also LDL, VLDL and the like gradually react, and it is difficult to obtain a clear terminal point of the reaction, and thus, the specificity of HDL by the use of this prior art method is not satisfactory.

DISCLOSURE OF THE INVENTION

The present inventors have found that amount of HDL cholesterol in an HDL-containing sample can be specifically determined without separating an aggregated substance by conducting an enzymatic reaction for determining the amount of cholesterol using a cholesterol reagent in the presence of a reagent for aggregating lipoproteins except HDL, such as LDL, VLDL and CM and completed the present invention based on this finding.

The present invention relates to a method of determining the amount of HDL cholesterol, which comprises reacting a HDL-containing sample with cholesterol hydrolase and cholesterol oxidase or cholesterol dehydrogenase in the presence of a reagent for aggregating lipoproteins except HDL, and determining the amount of hydrogen peroxide or reductive co-enzyme formed therein.

The method of the present invention can be applied to a body fluid containing HDL such as blood and urine.

An example of the method in the present invention will be described below.

As the first reagent, a nearly neutral buffer containing a reagent for aggregating lipoproteins except HDL is prepared. Further, as the second reagent, a buffer containing cholesterol esterase, cholesterol oxidase (or cholesterol dehydrogenase), peroxidase, 4-aminoantipyrine and a modified Trinder's reagent [or NAD(P)] is prepared. The modified Trinder's reagent may be incorporated into the first reagent. A body fluid sample is added in a fixed amount to the first reagent, and the mixture is heated, for example, at 37° C. for a few minutes to aggregate LDL, VLDL and CM. The second reagent is added to the mixture and the mixture is stirred for enzymatic reaction. At this time, when hydrogen peroxide is formed by cholesterol oxidase, an absorbance at a $\lambda$ maximum wavelength of a pigment formed from 4-aminoantipyrine and the modified Trinder's reagent by hydrogen peroxide and peroxidase is measured; when using the cholesterol dehydrogenase, the increase in the amount of NAD(P)H is measured through the absorbance at 300 to 500 nm, preferably 330 to 400 nm, for example, 340 nm. It is possible that diaphorase and tetrazolium salt are added to cause color development of a formazan pigment, and the amount of the formazan pigment is determined comparatively. The amount of HDL cholesterol is comparatively calculated by separately conducting the same procedure using a standard solution containing a fixed amount of cholesterol. It is also possible that the first and second, reagents are used in combination from the beginning, the body fluid sample is added thereto, and the mixture is heated, for example, at 37° C. for a few minutes to aggregate LDL, VLDL and CM, after which the enzymatic reaction is conducted.

The reagent for aggregating lipoproteins contains an aggregating agent and a divalent metal salt. Examples of the aggregating agent include heparin or its salt, phosphotungstic acid or its salt, dextran sulfuric acid or its salt, polyethylene glycol, sulfated cyclodextrin or its salt, sulfated oligosaccharide or its salt, and mixtures thereof. Examples of the cyclodextrin include $\alpha$-cyclodextrin, $\beta$-cyclodextrin and $\gamma$-cyclodextrin. Examples of the oligosaccharide include maltotriose, maltotetraose, maltopentaose, maltohexaose and maltoheptaose. Examples of the salts include salts of sodium, potassium, lithium, ammonium and magnesium. Examples of the divalent metal salt include salts of magnesium, calcium, manganese and nickel.

Preferable examples of the aggregating agent include 0.02 to 10 mM heparin having a molecular weight of 5,000 to 20,000 or its salt, 0.1 to 10 mM phosphotungstic acid having a molecular weight of 4,000 to 8,000 or its salt, 0.01 to 5 mM dextran sulfuric acid having a molecular weight of 10,000 to 500,000, 0.1 to 20 mM dextran sulfuric acid having a molecular weight of 1,000 to 10,000 or its salt, 0.3 to 100 mM polyethylene glycol (PEG) having a molecular weight of 4,000 to 25,000, 0.1 to 50 mM sulfated cyclodextrin having a molecular weight of 1,000 to 3,000 or its salt, 0.1 to 50 mM sulfated oligosaccharide having a molecular weight of 400 to 3,000 or its salt, and mixtures thereof. More preferable are 0.03 to 1 mM heparin having a molecular weight of 14,000 to 16,000 or its salt, 0.1 to 3 mM phosphotungstic acid having a molecular weight of 5,000 to 7,000 or its salt, 0.01 to 5 mM dextran sulfuric acid having a molecular weight of 150,000 to 250,000 or its salt, 0.1 to 10 mM dextran sulfuric acid having a molecular weight of 1,000 to 5,000 or its salt, 1.0 to 50 mM PEG having a molecular weight of 5,000 to 22,000, 0.1 to 10 mM sulfated cyclodextrin having a molecular weight of 1,000 to 2,000 or its salt, 0.1 to 10 mM sulfated oligosaccharide having a molecular weight of 400 to 2,000 or its salt, and mixtures thereof.

Examples of the divalent metal salt include salts of magnesium, calcium, manganese and nickel, the concentration of which being 0.1 to 50 mM. Preferable is the magnesium salt in the concentration of 0.1 to 50 mM.

Examples of the modified Trinder's reagent include N-ethyl-N-(3-methylphenyl)-N'-succinylethylenediamine (EMSE), N-ethyl-N-(3-methylphenyl)-N'-acetylethylenediamine, N,N-dimethyl-m-toluidine, N,N-disulfopropyl-3,5-dimethoxyaniline, N-ethyl-N-sulfopropyl-m-anisidine, N-ethyl-N-sulfopropylaniline, N-ethyl-N-sulfopropyl-3,5-dimethoxyaniline, N-sulfopropyl-3,5-dimethoxyaniline, N-ethyl-N-sulfopropyl-3,5-dimethylaniline, N-ethyl-N-sulfopropyl-m-toluidine, N-ethyl-N-(2-hydroxy-3-sulfopropyl)-m-anisidine, N-ethyl-N-(2-hydroxy-3-sulfopropyl)aniline, N-ethyl-N-(2-hydroxy-3-sulfopropyl)-3,5-dimethoxyaniline, N-(2-hydroxy-3-sulfopropyl)-3,5-dimethoxyaniline, N-ethyl-N-(2-hydroxy-3-sulfopropyl)-3,5-dimethylaniline, N-ethyl-N-(2-hydroxy-3-sulfopropyl)-m-toluidine, N-sulfopropylaniline, 3-hydroxy-2,4,6-triiodobenzoic acid and phenol.

Examples of the enzyme include commercial enzymes, namely, cholesterol esterase derived from a microorganism or an animal having the ability to hydrolyze cholesterol ester, cholesterol esterase such as lipoprotein lipase, cholesterol oxidase derived from a microorganism which catalyzes the oxidation of cholesterol to form hydrogen peroxide, and cholesterol dehydrogenase derived from a microorganism or an animal. In order to improve the specificity and the stability of the above-mentioned enzymes, the enzymes can be chemically modified by a group mainly composed of polyethylene glycol, a water-soluble oligosaccharide residue, a sulfopropyl group. An enzyme obtained by gene manipulation can also be used.

Since the system of the present invention includes an ordinary system to measure the cholesterol, a surfactant or a cholic acid which is often used to activate the cholesterol oxidase can also be employed. Also employed are various salts for dissolving globulin or the like. Examples of the surfactant include nonionic, anionic and cationic surfactants, and the concentration of which is 0 to 1%. Examples of the cholic acid include cholic acid, deoxycholic acid, taurocholic acid and chenodeoxycholic acid, and the concentration of which is 0 to 5%. Examples of the salts include sodium chloride, sodium sulfate, potassium chloride, potassium sulfate, magnesium chloride, magnesium sulfate, magnesium acetate, lithium chloride, lithium sulfate, ammonium chloride, ammonium sulfate, magnesium nitrate and calcium nitrate, and the concentration of which is 0 to 100 mM.

As the buffer, a tris buffer or a Good's buffer is preferably used in the concentration of 5 to 500 mM. The pH range is preferably 5 to 9.

The present invention will be illustrated specifically by referring to the following Examples.

BEST MODE FOR CARRYING OUT THE INVENTION

EXAMPLE 1

The amount of HDL cholesterol in the human serum was determined by the method of the present invention wherein the amount of HDL cholesterol is directly determined, a phosphotungstic acid-dextran sulfuric acid-Mg precipitation method [hereinafter simply referred to as "precipitation method"][precipitation using a Determiner-HDL (manufactured by Kyowa Medex Co., Ltd.)] (Clinical Chemistry, 1st edition, Ogi M., Itensha, p. 110, 1987) and a method using a cholic acid as described in Japanese Published Unexamined Patent Application No. 126,498/1988 (hereinafter referred to as "A-method").

Composition in the method of the present invention

First reagent

| | |
|---|---|
| phosphotungstic acid | 10 mg/ml (1.7 mM) |
| magnesium sulfate 7-hydrate | 7.5 mg/ml |
| EMSE | 0.3 mg/ml |
| sodium azide | 0.1 mg/ml |

Second reagent

| | |
|---|---|
| tris | 20 mM (pH 7) |
| 4-aminoantipyrine | 0.5 mg/ml |
| peroxidase | 30 U/ml |
| cholesterol esterase | 1 U/ml |
| cholesterol oxidase | 1 U/ml |

In the method of the present invention, 50 $\mu$l of a specimen was added to 2.25 ml of the first reagent, and the mixture was incubated at 37° C. for 5 minutes. At this time, an absorbance at 555 nm was once measured (E1). Then, 0.75 ml of the second reagent was added thereto, and the mixture was stirred. Five minutes later, the absorbance at the same wavelength was measured(E2). The amount of HDL cholesterol was determined using a standard solution containing 200 mg/dl cholesterol, and was calculated upon comparison of the (E2–E1) value.

In the pre cipita tion method, the amount of HDL cholesterol was determined using a Determiner-LTC (manufactured by Kyowa Medex Co., Ltd.) with Hitachi 7250 autoanalyzer after the completion of the centrifugation.

The results are shown in Table 1.

TABLE 1

|  | Method of the present invention | Precipitation method | A-method |
|---|---|---|---|
| Human serum 1 | 28 mg/dl | 24 mg/dl | 58 mg/dl |
| Human serum 2 | 39 | 38 | 79 |
| Human serum 3 | 57 | 56 | 82 |

The method of the present invention was closely correlated with the phosphotungstic acid-dextran sulfuric acid-Mg precipitation method which is ordinarily used at present as a method of determining the amount of HDL cholesterol.

EXAMPLE 2

Substantially the same procedure as in Example 1 (method of the present invention) was repeated except that the aggregating agent and divalent metal salt used in the first reagent were replaced with those having the following compositions A to I. Thirty serum specimens were measured using a Hitachi 7250 autoanalyzer (specimen—4 μl, first reagent—300 μl, second reagent—100 μl). The correlation between the method of the present invention and the precipitation method was examined using a coefficient of correlation (R).

Composition of the first reagent

| A. phosphotungstic acid | 10 mg/ml (1.7 mM) |
| magnesium sulfate 7-hydrate | 7.5 mg/ml |
| EMSE | 0.3 mg/ml |
| B. sodium dextran sulfate (MW = 4,000) | 7.5 mg/ml (1.9 mM) |
| magnesium sulfate 7-hydrate | 10 mg/ml |
| EMSE | 0.3 mg/ml |
| C. heparin sodium | 10 mg/ml (0.7 mM) |
| calcium chloride 2-hydrate | 10 mg/ml |
| EMSE | 0.3 mg/ml |
| D. phosphotungstic acid | 10 mg/ml (1.7 mM) |
| sodium dextran sulfate (MW = 200,000) | 7.5 mg/ml (1.9 mM) |
| magnesium sulfate 7-hydrate | 7.5 mg/ml |
| EMSE | 0.3 mg/ml |
| E. phosphotungstic acid | 10 mg/ml (1.7 mM) |
| heparin sodium | 7.5 mg/ml (0.5 mM) |
| magnesium sulfate 7-hydrate | 7.5 mg/ml |
| EMSE | 0.3 mg/ml |
| F. phosphotungstic acid | 10 mg/ml (1.7 mM) |
| PEG 6000 | 7.5 mg/ml (1.25 mW) |
| magnesium sulfate 7-hydrate | 7.5 mg/ml |
| EMSE | 0.3 mg/ml |
| G. PEG 6000 | 5 mg/ml (0.83 mM) |
| magnesium sulfate 7-hydrate | 5 mg/ml |
| EMSE | 0.3 mg/ml |
| H. sulfated α-cyclodextrin | 1 mg/ml (0.8 mM) |
| magnesium chloride 6-hydrate | 5 mg/ml |
| N-ethyl-N-(2-hydroxy-3-sulfopropyl)-m-toluidine | 0.6 mg/ml |
| I sulfated maltoheptaose | 2 mg/ml (0.6 mM) |
| magnesium chloride 6-hydrate | 5 mg/ml |
| N-ethyl-N-(2-hydroxy-3-sulfopropyl)-3,5-dimethoxyaniline | 0.7 mg/ml |

The results are shown in Table 2.

TABLE 2

|  | Coefficient of correlation |
|---|---|
| A. | R = 0.902 |
| B. | R = 0.859 |
| C. | R = 0.889 |
| D. | R = 0.923 |
| E. | R = 0.910 |
| F. | R = 0.909 |
| G. | R = 0.835 |
| H. | R = 0.911 |
| I. | R = 0.877 |

EXAMPLE 3

Substantially the same procedure as in Example 1 (method of the present invention) was repeated except that magnesium sulfate, calcium chloride, manganese chloride and nickel chloride were used as the divalent metal salt to be added to the first reagent and the concentration of the divalent metal salt was 30 mM. Thirty serum specimens were measured using a Hitachi 7250 autoanalyzer (specimen—4 μl, first reagent—300 μl, second reagent—100 μl). The correlation between the method of the present invention and the precipitation method was examined using a coefficient of correlation (R).

Composition

First reagent

| phosphotungstic acid | 10 mg/ml (1.7 mM) |
| divalent metal salt | 30 mM |
| EMSE | 0.3 mg/ml |
| sodium chloride | 5 mg/ml |
| sodium azide | 0.1 mg/ml |

Second reagent

| tris | 20 mM (pH 7) |
| 4-aminoantipyrine | 0.5 mg/ml |
| sodium cholate | 5 mg/ml |
| peroxidase | 30 U/ml |
| cholesterol esterase | 1 U/ml |
| cholesterol oxidase | 1 U/ml |

The results are shown in Table 3.

TABLE 3

| Divalent metal salt | Coefficient of correlation |
|---|---|
| magnesium sulfate | R = 0.914 |
| calcium chloride | R = 0.835 |
| manganese chloride | R = 0.816 |
| nickel chloride | R = 0.798 |

EXAMPLE 4

Cholesterol esterase and cholesterol oxidase chemically modified with polyethylene glycol (molecular weight 6,000) using Sun Bright 4001 (manufactured by Nippon Oils and Fats Co., Ltd.) were prepared respectively. Substantially the same procedure as in Example 1 (method of the present invention) was repeated using the first and second reagents having the following composition in the presence of these enzymes. Thus, the amount of HDL cholesterol in the human serum was determined. Further, the amount of HDL cholesterol in the human serum was determined through the precipitation method.

Composition
First reagent

| | |
|---|---|
| phosphotungstic acid | 10 mg/ml (1.7 mM) |
| sodium dextran phosphate (MW = 4,000) | 7.5 mg/ml (1.9 mM) |
| magnesium sulfate 7-hydrate | 7.5 mg/ml |
| EMSE | 0.3 mg/ml |
| sodium chloride | 5 mg/ml |
| sodium azide | 0.1 mg/ml |
| ascorbic acid oxidase | 1 U/ml |

Second reagent

| | |
|---|---|
| tris | 20 mM (pH 7) |
| 4-aminoantipyrine | 0.5 mg/ml |
| sodium cholate | 5 mg/ml |
| peroxidase | 30 U/ml |
| modified cholesterol esterase | 1 U/ml |
| modified cholesterol oxidase | 1 U/ml |

The enzyme was chemically modified by dissolving the enzyme (10 mg/ml) into 20 mM phosphate buffer (pH 8), cooling the solution to 5+ C. Then, 20 equivalents of Sun Bright 4001 was added to the solution and dissolved. The reaction was conducted at 5° C. for 4 hours. The chemically modified enzyme thus obtained was used as such as an enzyme solution without purification or separation.

The results are shown in Table 4.

TABLE 4

| | Method of the present invention | Precipitation method |
|---|---|---|
| Human serum 1 | 26 mg/dl | 24 mg/dl |
| Human serum 2 | 37 | 38 |
| Human serum 3 | 56 | 56 |

EXAMPLE 5

The specimen (50 μl), the concentration of HDL cholesterol of which had been determined to be 38.9 mg/dl through the phosphotungstic acid-dextran sulfuric acid-Mg precipitation method, was added to 3 ml of a reagent having the following composition. After 20 seconds, an absorbance at 555 nm was measured (El).

Composition
Reagent

| | |
|---|---|
| piperazine-1,4-bis(2-ethane sulfonic acid) [manufactured by Dojin Laboratories] | 3 mg/ml (9.9 mM) (pH 7) |
| EMSE | 0.3 mg/ml |
| sodium dextran sulfate | 0.7 mg/ml (1.4 μM) |
| magnesium sulfate 7-hydrate | 7 mg/ml |
| 4-aminoantipyrine | 0.5 mg/ml |
| peroxidase | 5 U/ml |
| cholesterol esterase | 1 U/ml |
| cholesterol oxidase | 5 U/ml |

The mixture was then incubated at 37° C. for 5 minutes, and an absorbance at the same wavelength was immediately measured (E2). The concentration of HDL cholesterol was calculated by conducting the same procedure using a standard solution containing 200 mg/dl cholesterol and comparing the (E2-E1) value. Consequently, the concentration of HDL cholesterol was calculated as 39.1 mg/dl, which coincided approximately with the results obtained through the precipitation method.

EXAMPLE 6

Substantially the same procedure as in Example 4 was repeated except that the following enzymes (1), (2) and (3) and 50 μl of the specimen, the concentration of HDL cholesterol of which had been determined to be 38.9 mg/dl through the phosphotungstic acid-dextran sulfuric acid-magnesium precipitation method, were used.

(1) cholesterol esterase and cholesterol oxidase which had been chemically modified using a reagent for modifying dextran, T40,TCT-activated (manufactured by Boehringer)

(2) cholesterol esterase and cholesterol oxidase which had been chemically modified using a reagent for modifying polyurethane, Polyurethane P4000-activated (manufactured by Boehringer)

(3) cholesterol esterase and cholesterol oxidase which had been chemically modified using 1,3-propanesultone The chemical modification was conducted as follows.

With respect (1) and (2), the enzyme (10 mg/ml) was dissolved in 20 mM phosphate buffer (pH 8), and the solution was cooled to 5° C. Then, 20 equivalents of T40,TCT-activated [for enzyme (1)] or Polyurethane P4000-activated [for enzyme (2)] was added to the solution and dissolved. The reaction was conducted at 5° C. for 4 hours.

With respect to enzyme (3), the enzyme (10 mg/ml) was dissolved in 20 mM phosphate buffer (pH 8). Dimethylformamide containing 20 equivalents of 1,3-propanesultone (10 mg/ml) was added to the solution and dissolved. The reaction was conducted at 37° C. for 24 hours.

The chemically modified enzymes (1), (2) and (3) thus obtained were used as such as enzyme solutions without conducting purification or separation.

Consequently, the concentration of HDL cholesterol were (1) 39.7 mg/dl, (2) 38.2 mg/dl and (3) 39.0 mg/dl which coincided approximately with the results obtained using the precipitation method.

Industrial Applicability

The present invention provides a method of determining an amount of HDL cholesterol which method is simple in that it requires no intricate fractionation and separation procedures.

We claim:

1. A kit for determining the amount of cholesterol in a high-density lipoprotein (HDL) without separating lipoproteins from an HDL-containing sample, which comprises:

i) a first reagent for aggregating lipoproteins except HDL, ii) a second reagent comprising cholesterol esterase, and either cholesterol oxidase or cholesterol dehydrogenase, and iii) a third reagent for determining the amount of hydrogen peroxide or reductive co-enzyme formed therein.

2. The kit according to claim 1, wherein at least one of the first, second and third reagents further contains a surfactant or cholic acid.

3. A kit for determining the amount of cholesterol in a high-density lipoprotein (HDL) without separating lipoproteins from an HDL-containing sample, which comprises:

(A) a first reagent comprising a composition for aggregating lipoproteins except HDL; and a composition for determining the amount of hydrogen peroxide or reductive co-enzyme formed therein, and (B) a second reagent comprising cholesterol esterase, and either of cholesterol oxidase or cholesterol dehydrogenase.

4. The kit according to claim 3, wherein at least one of the first and second reagents further contains a surfactant or cholic acid.

5. A kit for determining the amount of cholesterol in a high-density lipoprotein (HDL) without separating lipoproteins from an HDL-containing sample, which comprises:

a reagent comprising a composition for aggregating lipoproteins except HDL, cholesterol esterase, and either of cholesterol oxidase or cholesterol dehydrogenase; and a composition for determining the amount of hydrogen peroxide or reductive co-enzyme formed therein.

6. The kit according to claim 5, wherein said reagent further contains a surfactant or cholic acid.

7. A kit for determining the amount of cholesterol in a high-density lipoprotein (HDL) without separating lipoproteins from an HDL-containing sample, which comprises:

(A) a first reagent for determining the amount of hydrogen peroxide or reductive co-enzyme formed therein, and (B) a second reagent comprising a composition for aggregating lipoproteins except HDL, cholesterol esterase, and either of cholesterol oxidase or cholesterol dehydrogenase.

8. The kit according to claim 7, wherein at least one of the first and second reagents further contains a surfactant or cholic acid.

9. A kit for determining the amount of cholesterol in a high-density lipoprotein (HDL) without separating lipoproteins from an HDL-containing sample, which comprises:

(A) a first reagent comprising a portion of a composition for aggregating lipoproteins except HDL; and a composition for determining the amount of hydrogen peroxide or reductive co-enzyme formed therein, and (B) a second reagent comprising the remaining portion of said composition for aggregating lipoproteins except HDL, cholesterol esterase, and either of cholesterol oxidase or cholesterol dehydrogenase.

10. The kit according to claim 9, wherein at least one of the first and second reagents further contains a surfactant or cholic acid.

11. A kit for determining the amount of cholesterol in a high-density lipoprotein (HDL) without separating lipoproteins from an HDL-containing sample, which comprises:

(A) a first reagent comprising a composition for aggregating lipoproteins except HDL; and a portion of a composition for determining the amount of hydrogen peroxide or reductive co-enzyme formed therein, and (B) a second reagent comprising cholesterol esterase, and either of cholesterol oxidase or cholesterol dehydrogenase; and the remaining portion of a composition for determining the amount of hydrogen peroxide or reductive co-enzyme formed therein.

12. The kit according to claim 11, wherein at least one of the first and second reagents further contains a surfactant or cholic acid.

13. A kit for determining the amount of cholesterol in a high-density lipoprotein (HDL) without separating lipoproteins from an HDL-containing sample, which comprises:

(A) a first reagent comprising a portion of a composition for determining the amount of hydrogen peroxide or reductive co-enzyme formed therein, and (B) a second reagent comprising a composition for aggregating lipoproteins except HDL, cholesterol esterase, and either of cholesterol oxidase or cholesterol dehydrogenase; and a composition comprising the remaining portion of the composition for determining the amount of hydrogen peroxide or reductive co-enzyme formed therein.

14. The kit according to claim 13, wherein at least one of the first and second reagents further contains a surfactant or cholic acid.

15. The kit of claim 1, 3, 5, 7, 9, 11 or 13, wherein the reagent for aggregating lipoproteins except HDL comprises an aggregating agent and a divalent metal salt.

16. The kit of claim 15, wherein said aggregating agent is selected from the group consisting of heparin, phosphotungstic acid, dextran sulfuric acid, sulfated cyclodextrin, sulfated oligosaccharide salts thereof, mixtures thereof; and polyethylene glycol.

17. The kit of claim 16, wherein the cyclodextrin is selected from the group consisting of alpha-cyclodextrin, beta-cyclodextrin and gamma-cyclodextrin.

18. The kit of claim 16, wherein said oligosaccharide is selected from the group consisting of maltotriose, maltotetraose, maltopentaose, maltohexaose and maltoheptaose.

19. The kit of claim 15, wherein said salt is selected from the group consisting of sodium, potassium, lithium, ammonium and magnesium, and said divalent metal salt is selected from the group consisting of magnesium, calcium, manganese, and nickel.

20. The kit of claim 1, 3, 5, 7, 9, 11 or 13, wherein said lipoproteins except HDL are selected from the group consisting of LDL, VLDL and CM.

21. The kit of claim 1 or 7, wherein said reagent for determining the amount of hydrogen peroxide comprises peroxidase, 4-aminoantipyrine and a modified Trinder's agent.

22. The kit of claim 3, 5, 9, 11 or 13, wherein said composition for determining the amount of hydrogen peroxide comprises peroxidase, 4-aminoantipyrine and a modified Trinder's agent.

23. The kit of claim 1 or 7, wherein the reagent for determining the amount of reductive co-enzyme formed comprises a composition for determining an increase in the amount of NAD(P)H.

24. The kit of claim 3, 5, 9, 11 or 13, wherein said composition for determining the amount of reductive co-enzyme formed comprises a composition for determining an increase in the amount of NAD(P)H.

25. The kit of claim 24, wherein said composition comprises diaphorase and tetrazolium salt.

26. The kit of claim 11, wherein said second reagent comprises tris, 4-aminoantipyrine, peroxidase, cholesterol esterase, cholesterol oxidase.

27. The kit of claim 26, wherein the first reagent is selected from the group consisting of:

(A) phosphotungstic acid, magnesium sulfate 7-hydrate and EMSE;

(B) sodium dextran sulfate (MW=4,000), magnesium sulfate 7-hydrate and EMSE;

(C) heparin sodium, calcium chloride 2-hydrate and EMSE;

(D) phosphotungstic acid, sodium dextran sulfate (MW=200,000), magnesium sulfate 7-hydrate and EMSE;

(E) phosphotungstic acid, heparin sodium, magnesium sulfate 7-hydrate and EMSE;

(F) phosphotungstic acid, PEG 6000, magnesium sulfate 7-hydrate and EMSE;

(G) PEG 6000, magnesium sulfate 7-hydrate and EMSE;

(H) sulfated α-cyclodextrin, magnesium chloride 6-hydrate and N-ethyl-N-(2-hydroxy-3-sulfopropryl)-m-toluidine; and (I) sulfated maltoheptaose, magnesium chloride 6-hydrate and N-ethyl-N-(2-hydroxy-3-sulfopropyl)-3,5-dimethoxyaniline.

28. The kit of claim 11, wherein the first reagent comprises phosphotungstic acid, divalent metal salt, EMSE, sodium chloride and sodium azide; and wherein the second reagent comprises tris, 4-aminoantipyrine, sodium cholate, peroxidase, cholesterol esterase and cholesterol oxidase.

29. The kit of claim 11, wherein the first reagent comprises phosphotungstic acid, sodium dextran phosphate (MW=4,000), magnesium sulfate 7-hydrate, EMSE, sodium chloride, sodium azide and ascorbic acid oxidase; and wherein the second reagent comprises tris, 4-aminoantipyrine, sodium cholate, peroxidase, modified cholesterol esterase and modified cholesterol oxidase.

30. The kit of claim 5, wherein the reagent comprises piperazine-1,4-bis(2-ethane sulfonic acid), EMSE, sodium dextran sulfate, magnesium sulfate 7-hydrate, 4-aminoantipyrine, peroxidase, cholesterol esterase and cholesterol oxidase.

31. A kit for determining the amount of cholesterol in a high-density lipoprotein (HDL) without separating lipoproteins from an HDL-containing sample, which comprises:

i) means for aggregating lipoproteins except HDL, ii) cholesterol esterase, and either cholesterol oxidase or cholesterol dehydrogenase, and iii) means for determining the amount of hydrogen peroxide or reductive co-enzyme formed therein.

32. The kit according to claim 31, wherein the kit comprises:

(A) a first reagent comprising means for aggregating lipoproteins except HDL, (B) a second reagent comprising cholesterol esterase, and either of cholesterol oxidase or cholesterol dehydrogenase, and (C) a third reagent comprising means for determining the amount of hydrogen peroxide or reductive co-enzyme formed therein.

33. A kit for determining the amount of cholesterol in a high-density lipoprotein (HDL) without separating lipoproteins from HDL-containing sample, which comprises:

(A) a first reagent for aggregating lipoproteins except HDL, and (B) a second reagent comprising cholesterol esterase, and either of cholesterol oxidase or cholesterol dehydrogenase; and a composition for determining the amount of hydrogen peroxide or reductive co-enzyme formed therein.

34. The kit according to claim 33, wherein at least one of the first and second reagents further contains a surfactant or cholic acid.

35. The kit of claim 33, wherein the reagent for aggregating lipoproteins except HDL comprises an aggregating agent and a divalent metal salt.

36. The kit of claim 33, wherein said lipoproteins except HDL are selected from the group consisting of LDL, VLDL and CM.

37. The kit of claim 33, wherein said reagent comprising cholesterol esterase, and either cholesterol oxidase or cholesterol dehydrogenase, comprises a buffer comprising peroxidase, 4-aminoantipyrine and a modified Trinder's agent.

38. The kit of claim 33, wherein the composition for determining the amount of hydrogen peroxide comprises peroxidase, 4-aminoantipyrine and the modified Trinder's agent.

39. The kit of claim 33, wherein the composition for determining the amount of reductive co-enzyme formed comprises a composition for determining an increase in the amount of NAD(P)H.

40. The kit of claim 39, wherein said composition comprises diaphorase and tetrazolium salt.

* * * * *